United States Patent
Smith et al.

(10) Patent No.: US 8,940,915 B2
(45) Date of Patent: Jan. 27, 2015

(54) SOLVENT FOR RECOVERY OF MALEIC ANHYDRIDE FROM A GAS STREAM

(75) Inventors: William Alan Smith, Spring, TX (US); Yury Chernyak, Spring, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 0 days.

(21) Appl. No.: 14/004,710

(22) PCT Filed: May 3, 2012

(86) PCT No.: PCT/US2012/036235
§ 371 (c)(1),
(2), (4) Date: Sep. 12, 2013

(87) PCT Pub. No.: WO2012/154479
PCT Pub. Date: Nov. 15, 2012

(65) Prior Publication Data
US 2014/0081036 A1    Mar. 20, 2014

Related U.S. Application Data

(60) Provisional application No. 61/484,994, filed on May 11, 2011.

(51) Int. Cl.
*C07D 307/60* (2006.01)
*C08F 222/02* (2006.01)
*C08F 222/08* (2006.01)

(52) U.S. Cl.
CPC ............ *C07D 307/60* (2013.01); *C08F 222/02* (2013.01); *C08F 222/08* (2013.01)
USPC .......................................................... 549/477

(58) Field of Classification Search
CPC .................................................... C07D 307/60
USPC ....................................................... 549/477
See application file for complete search history.

(56) References Cited

U.S. PATENT DOCUMENTS

| | | | |
|---|---|---|---|
| 3,741,943 | A | 6/1973 | Sekmakas et al. |
| 3,891,680 | A | 6/1975 | Katsumoto et al. |

(Continued)

FOREIGN PATENT DOCUMENTS

| | | |
|---|---|---|
| DE | 2444824 | 4/1976 |
| EP | 0459543 | 12/1991 |

(Continued)

OTHER PUBLICATIONS

JP-B-35-7460; Jun. 6, 1960; AIPN Online English Machine Translation; Mar. 27, 2014).*

(Continued)

*Primary Examiner* — Noble Jarrell
*Assistant Examiner* — John Mauro
(74) *Attorney, Agent, or Firm* — Huntsman International LLC

(57) ABSTRACT

A process is described for producing crude maleic anhydride from a reactor effluent stream containing maleic anhydride. The reactor effluent stream is contacted with a solvent having a normal boiling point between about 250° C. and about 350° C., solubility of fumaric acid at least about 0.06 wt % at 60° C., solubility of maleic anhydride at least about 10 wt % at 60° C., solubility in water no higher than about 100 mg/L, density different from the density of water by at least about 0.020 g/mL, and water soluble hydrolysis products with molecular weight no higher than the molecular weight of pentanol. The solvent may be non-cyclic, non-aromatic, linear, and/or branched, and may have the general structure $R_1COOR_2COOR_3$, wherein $R_1$ and $R_3$ are each linear or branched $C_3$ to $C_5$ groups and $R_2$ is a linear or branched $C_3$ to $C_8$ group.

15 Claims, 1 Drawing Sheet

(56) References Cited

U.S. PATENT DOCUMENTS

| | | |
|---|---|---|
| 4,118,403 A | 10/1978 | White |
| 5,069,687 A | 12/1991 | Bertola et al. |
| 5,631,387 A | 5/1997 | Brown et al. |
| 5,718,808 A | 2/1998 | Baiel et al. |

FOREIGN PATENT DOCUMENTS

| | | | |
|---|---|---|---|
| EP | 0815098 | | 1/1998 |
| GB | 1443411 | | 7/1976 |
| JP | 35-7460 B | * | 6/1960 |

OTHER PUBLICATIONS

Sigma Aldrich Catalog 2014; Various Excerpts.*

Food and Agriculture Organization of the United Nations—Excerpt—http://www.fao.org/ag/agn/jecfa-flav/details.html?flavId=2876 (2014).*

* cited by examiner

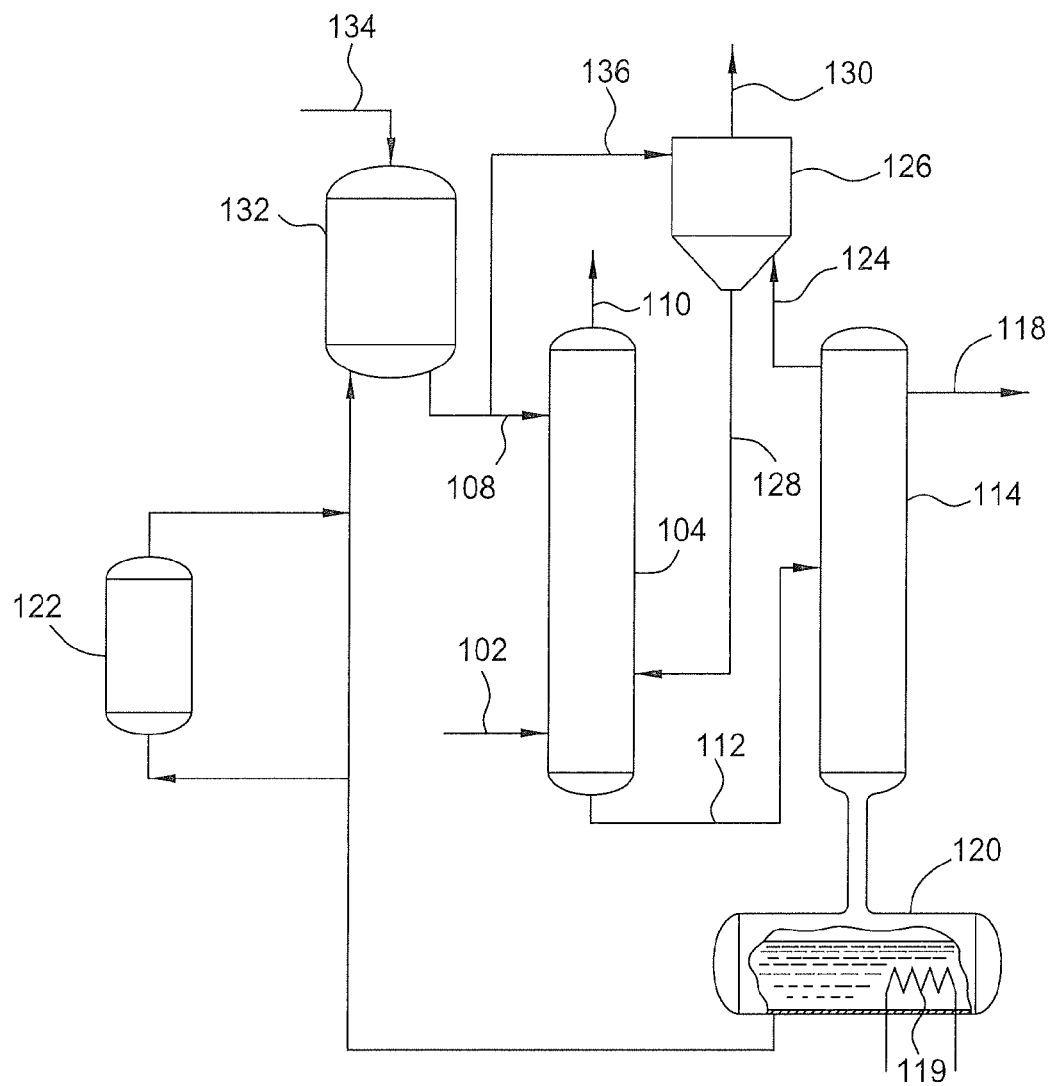

US 8,940,915 B2

SOLVENT FOR RECOVERY OF MALEIC ANHYDRIDE FROM A GAS STREAM

BACKGROUND OF THE INVENTION

1. Field of the Invention

Embodiments described herein generally relate to processes for manufacturing maleic anhydride. Specifically, processes and solvents for recovering a crude maleic anhydride stream from a reactor effluent are described.

2. Description of the Related Art

Maleic anhydride (cis-butanedioic anhydride) is used alone or in combination with other acids in the manufacture of alkyd and polyester resins. It is also a versatile intermediate for chemical synthesis. Global demand for maleic anhydride in 2009 was approximately 1.7 MT (million metric tons), with demand growth estimated by some at about 4% through 2020.

Maleic anhydride is prepared commercially by contacting a feed gas comprising molecular oxygen and a suitable hydrocarbon (e.g., n-butane or butene) with a vanadium-phosphorus-oxygen catalyst to partially oxidize the hydrocarbon and produce maleic anhydride. Hydrocarbons are converted to maleic anhydride by passing the feed gas through a reactor containing a fixed or fluidized bed of catalyst. The reaction product gas which is produced contains maleic anhydride together with oxidation by-products such as CO, $CO_2$, water vapor, acrylic and acetic acids and other by-products, along with inert gases present in air when air is used as the source of molecular oxygen.

The prior art discloses a number of methods of isolating and recovering maleic anhydride from the reaction product gas. For example, the maleic anhydride can be recovered by direct condensation from the reaction product gas or by scrubbing the gas with water and dehydrating the resulting aqueous mixture by azeotropic distillation with xylene. However, due to increased product yields, the preferred method of recovery comprises selectively absorbing the maleic anhydride in a suitable solvent and subsequently stripping the maleic anhydride from the resulting absorption liquor to obtain crude product.

U.S. Pat. No. 4,118,403 (White) discloses contacting the reaction product gas with an organic solvent in an absorber column so that the maleic anhydride, as well as some of the oxidation by-products, are absorbed in the solvent. The solvent comprises a dialkyl phthalate having 2 to 8 carbon atoms in each alkyl chain (e. g., dibutyl phthalate), and from about 0.5 to about 10 weight percent phthalic anhydride. U.S. Pat. No. 3,891,680 describes carrying out the washing operation in esters formed from phthalic acid with C4-C5 alcohols. According to German O.S.2,444,824, dibenzylbenzol is used as the wash fluid. British Pat. No. 1,443,411 describes polymethylbenzophenone as the wash fluid.

European Published Patent Application 0 459 543 A1 discloses a process for recovery of maleic anhydride from reaction mixtures resulting from the catalytic oxidation of butane, butene, mixtures of hydrocarbons containing four carbon atoms, or benzene in which the gaseous reaction mixture containing maleic anhydride is contacted with an organic solvent such as dibutyl phthalate to absorb maleic anhydride contained in the reaction mixture. The maleic anhydride-enriched solvent is contacted with a gas of low relative humidity at a pressure of between 0.01 and 2.0 bar and at a temperature above 80° C. to remove water and then continues to a separation step in which maleic anhydride is stripped from the solvent, whereupon the resulting lean solvent is washed with water to remove contaminants before being recycled to the adsorption zone.

European Patent EP 0 815 098 B1 claims that the solvent preferably comprises a dialkyl phthalate compound having from two to eight carbon atoms in each alkyl chain. Suitable dialkyl phthalate compounds include: dimethyl phthalate, diethyl phthalate, dipropyl phthalate, diisopropyl phthalate, dibutyl phthalate, diisobutyl phthalate, dimethyl dihydrophthalate, diethyl dihydrophthalate, dipropyl dihydrophthalate, diisopropyl dihydrophthalate, dibutyl dihydrophthalate, diisobutyl dihydrophthalate, dimethyl tetrahydrophthalate, diethyl tetrahydrophthalate, dipropyl tetrahydrophthalate, diisopropyl tetrahydrophthalate, dibutyl tetrahydrophthalate, and diisobutyl tetrahydrophthalate, dibutyl phthalate being the most preferred maleic anhydride-absorbing solvent.

Although extraction of maleic anhydride using phthalates as a solvent is widely taught and practiced today, the cost of phthalates such as dibutyl phthalate is increasing. Thus, there is a need for a lower cost maleic anhydride extraction process and solvent.

SUMMARY OF THE INVENTION

Embodiments described herein include a process for producing crude maleic anhydride by contacting a reactor effluent stream containing maleic anhydride with a solvent having a normal boiling point between about 250° C. and about 350° C., solubility of fumaric acid at least about 0.06 wt % at 60° C., solubility of maleic anhydride at least about 10 wt % at 60° C., solubility in water no higher than about 100 mg/L, density different from the density of water by at least about 0.020 g/mL, and water soluble hydrolysis products with molecular weight no higher than the molecular weight of pentanol. The solvent may be non-cyclic, non-aromatic, linear, and/or branched, and may have the general structure $R_1COOR_2COOR_3$, wherein $R_1$ and $R_3$ are each linear or branched $C_3$ to $C_5$ groups, and $R_2$ is a linear or branched $C_3$ to $C_8$ group.

In another embodiment, a process for producing crude maleic anhydride includes contacting a reactor effluent stream comprising maleic anhydride with a solvent having the general formula $R_1COOR_2COOR_3$, wherein $R_1$ and $R_3$ are each linear or branched $C_3$ to $C_5$ groups and $R_2$ is a linear or branched $C_3$ to $C_8$ group.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 1 is a process flow diagram summarizing a process for recovering maleic anhydride.

DETAILED DESCRIPTION

The inventors have discovered new solvents that may be used to extract a crude maleic anhydride stream from a reactor effluent. Suitable solvents have normal boiling point between about 250° C. and about 350° C., are easily separable from maleic anhydride, dissolve fumaric acid at least about 0.06 wt % at 60° C., dissolve maleic anhydride at least about 10 wt % at 60° C., are soluble in water at 100 mg/L or less, and have a difference in density from water by at least about 0.020 g/mL, either above or below.

Maleic anhydride is extracted from a reaction effluent stream using a solvent extraction process. FIG. 1 is a process flow diagram summarizing a process for recovering maleic anhydride. A gaseous reactor effluent stream comprising maleic anhydride is introduced to the bottom of an absorber column 104 through feed line 102. A solvent is introduced to the absorber column 104 near the top of the column through a solvent feed line 108. The reactor effluent stream 102 is contacted with the solvent in the absorber column 104, transferring maleic anhydride from the reactor effluent to the solvent. The extracted gaseous stream is vented from the absorber column 104 through a vent line 110, and the rich solvent containing maleic anhydride is withdrawn from the absorber column through a rich solvent line 112 near the absorber bottom.

The rich solvent is introduced to a stripping column 114 near the middle thereof. Crude maleic anhydride is withdrawn from the stripping column 114 near a middle or upper portion thereof through a crude maleic anhydride line 118. The stripping column 114 typically operates at a pressure below atmospheric pressure, and a crude maleic anhydride stream may be extracted as a gas or a liquid. In embodiments wherein the crude maleic anhydride is extracted as a gas, the crude maleic anhydride may be condensed in a condenser (not shown) to yield a liquid crude maleic anhydride stream. In some embodiments, the stripping column 114 is refluxed by condensing an overhead stream and returning a portion of the condensate to the top of the stripping column 114. In some embodiments, the stripping column 114 may be totally refluxed. The solvent is reboiled in a reboiler 120, with heat applied through heat exchanger 119, and solvent is removed from the reboiler, cooled, and recycled to the absorber column 104. The recycled solvent may also be filtered and stored in a storage tank 132.

Some solvent decomposes within the process, so fresh solvent may be added to the solvent storage tank 132 through a solvent make-up line 134. A slip stream of recycled solvent may be purified by distillation or aqueous extraction in purifier 122.

Low boiling components of the reactor effluent stream extracted into the solvent in the absorber column 104, or produced as byproducts of the extraction process, are vented from the stripping column 114 through a vent line 124. Maleic anhydride that exits through the vent line 124 is recovered by solvent extraction in a scrubber 126 at conditions similar to those in the condenser, and the scrubbed solvent stream containing maleic anhydride is returned to the absorber column 104 through a scrubbed solvent line 128. The low boiling components not removed by the scrubber exit the process through a scrubber vent line 130. Solvent for the scrubbing process is fed to the scrubber 126 from the solvent storage tank 132 through a lean solvent line 136.

Maleic anhydride is typically produced by oxidizing a gas-phase hydrocarbon such as n-butane or butene in a reactor over a fixed or fluidized bed of vanadium-phosphorus-oxygen catalyst. Byproducts of the reaction include CO, $CO_2$, water vapor, acetic acid, maleic acid, and acrylic acid. These contaminants, and others such as fumaric acid, are further produced in the purification process by reactions of maleic anhydride, or any of the above byproducts, with water. When air is used as an oxygen source, the reactor effluent gas also includes inert gases from the air. Small quantities of $C_5$ in the $C_4$ feedstock are also partially oxidized to CO, $CO_2$, water vapor, and other impurities, which are removed with the absorber vent stream.

Solvents used for the extraction process are generally esters due to their relative inactivity with respect to maleic anhydride and solubility of maleic anhydride in esters. Because organic acids are formed in the circulating solvent, and these acids are extracted and excluded in a byproduct stream, solvents with low water solubility are preferred to avoid large losses of solvent. Solubility of the solvent in water less than about 100 mg/L is generally acceptable, but higher solubility solvents are usable if solvent loss can be tolerated.

It is preferred that the solvent be readily separable from maleic anhydride itself. The common process for purifying crude maleic anhydride is a distillation process, so a solvent having a normal boiling point substantially different, usually higher, than maleic anhydride is preferred. Maleic anhydride has a normal boiling point of 202° C., so a solvent with normal boiling point of at least about 250° C. is typically used. The solvent may have a boiling point between about 250° C. and about 350° C., such as between about 280° C. and about 350° C., for example between about 300° C. and about 340° C., may be used. In one embodiment, the solvent has a normal boiling point of about 305° C.

When esters and diesters are used as a solvent to extract maleic anhydride, a portion of the solvent may be hydrolyzed during the solvent extraction process. The high temperatures and presence of water decomposes the ester into its corresponding carboxylic acid and alcohol components. It is preferred that these components of the solvent be readily separable from maleic anhydride in the solvent extraction process. In one example, the alcohol hydrolysis byproducts are no heavier than pentanol, which may be removed from the process, for example, in the vent line 130 or by aqueous extraction in purifier 122. The acid byproducts are preferably soluble, at least partially, in water and in the solvent itself, so a portion of the acid byproduct leaves the process with water, while the rest recycles.

Byproducts of the maleic anhydride reaction are mentioned above. A solvent usable for maleic anhydride extraction generally has at least some ability to dissolve these byproducts. In particular, preferred solvents will dissolve fumaric acid to at least 0.06 wt % at 60° C. The byproducts are generally removed in the stripping process and the solvent purification process.

Solvents described herein that are suitable for maleic anhydride may be non-cyclic esters and diesters. Esters and diesters suitable for maleic anhydride extraction may be non-aromatic, linear, or branched. One class of suitable solvents having one or more of the aforementioned characteristics has the general structure $R_1COOR_2COOR_3$, wherein $R_1$, and $R_3$ are each linear or branched $C_3$ to $C_5$ groups, and $R_2$ is a linear or branched $C_3$ to $C_8$ group. In one embodiment, di-n-butyl adipate may be used as an effective solvent. Other solvents that may be used include di-t-butyl adipate, di-isobutyl adipate, and dipropyl suberate. In some embodiments, a mixture of solvents may be used.

Compounds containing halogens are usually avoided because halogens have unfavorable effects on stainless steel, but if stainless steel is replaced with alloys resistant to attack by halogens, such as suitable varieties of Monel, Inconel, or Hastelloy, halogen-containing solvents may be considered.

Di-n-butyl adipate, referred to hereafter as dibutyl adipate, is a suitable solvent for maleic anhydride extraction. Properties of dibutyl adipate with respect to the maleic anhydride extraction process are given in Table 1.

TABLE 1

| Normal Boiling Point | 305° C. |
|---|---|
| Solubility of Fumaric Acid | about 0.15 wt % at 60° C. |
| Solubility of Maleic Anhydride | >20 wt % at 60° C. |
| Solubility in Water | 35 mg/L at 25° C. |
| Specific Gravity | 0.962 g/mL at 25° C. |

Hydrolysis products of dibutyl adipate are butanol and adipic acid. Butanol is removed overhead in the vent line 130 or by aqueous extraction in purifier 122. Adipic acid is soluble both in water and in dibutyl adipate. Dibutyl adipate has the added benefit that neither dibutyl adipate nor any of its hydrolysis products is toxic.

While the foregoing is directed to embodiments of the present invention, other and further embodiments of the invention may be devised without departing from the basic scope thereof, and the scope thereof is determined by the claims that follow.

The invention claimed is:

1. A process for producing crude maleic anhydride, comprising:
   contacting a reactor effluent stream comprising maleic anhydride with a non-cyclic di-ester solvent having a normal boiling point between about 250° C. and about 350° C., solubility of fumaric acid at least about 0.06 wt % at 60° C., solubility of maleic anhydride at least about 10 wt % at 60° C., solubility in water no higher than about 100 mg/L, a density different from a density of water by at least 0.020 g/mL, and a water soluble hydrolysis product with molecular weight no higher than the molecular weight of pentanol.

2. The process of claim 1, wherein the solvent is linear.

3. The process of claim 1, wherein the solvent is an adipate.

4. The process of claim 1, wherein the solvent has the structure $R_1OOR_2OOR_3$, wherein $R_1$ and $R_3$ are each linear or branched $C_3$ to $C_5$ groups and $R_2$ is a linear or branched $C_3$ to $C_8$ group.

5. The process of claim 1, wherein the solvent has a density that is different from a density of water by at least about 0.025 g/mL.

6. The process of claim 1, wherein the solvent has a water soluble hydrolysis product that is an alcohol.

7. The process of claim 1, wherein the water soluble hydrolysis product is an alcohol.

8. The process of claim 1, wherein the solubility of maleic anhydride is at least about 15 wt %.

9. The process of claim 1, wherein the solubility of maleic anhydride is at least about 18 wt %.

10. The process of claim 1, wherein the solvent has a normal boiling point between about 280° C. and about 350° C.

11. The process of claim 1, wherein the normal boiling point is between about 300° C. and about 330° C.

12. The process of claim 1, wherein the solvent is dibutyl adipate.

13. The process of claim 1, wherein an acid byproduct of hydrolysis of the solvent is soluble in the solvent.

14. A process for producing crude maleic anhydride, comprising:
    contacting a reactor effluent stream comprising maleic anhydride with a non-cyclic di-ester solvent having a normal boiling point between about 280° C. and about 350° C., solubility of fumaric acid at least about 0.06 wt % at 60° C., solubility of maleic anhydride at least about 18 wt % at 60° C., solubility in water no higher than about 100 mg/L, and density different from the density of water by at least about 0.020 g/mL.

15. A process for producing crude maleic anhydride, comprising:
    contacting a reactor effluent stream comprising maleic anhydride with a non-aromatic di-ester solvent having a normal boiling point between about 280° C. and about 350° C., solubility of fumaric acid at least about 0.06 wt % at 60° C., solubility of maleic anhydride at least about 18 wt % at 60° C., solubility in water no higher than about 100 mg/L, and a water soluble hydrolysis product with molecular weight no higher than the molecular weight of pentanol.

* * * * *